US011957638B2

United States Patent
Solana et al.

(10) Patent No.: US 11,957,638 B2
(45) Date of Patent: Apr. 16, 2024

(54) SUCTION ASSEMBLY

(71) Applicant: THERABODY, INC., Los Angeles, CA (US)

(72) Inventors: Jaime Sanchez Solana, Los Angeles, CA (US); Mandar Deshmukh, Los Angeles, CA (US); Eduardo Merino, Los Angeles, CA (US); Tiki Ho, Los Angeles, CA (US)

(73) Assignee: Therabody, Inc., Los Angeles, CA (US)

( * ) Notice: Subject to any disclaimer, the term of this patent is extended or adjusted under 35 U.S.C. 154(b) by 0 days.

(21) Appl. No.: 17/711,590

(22) Filed: Apr. 1, 2022

(65) Prior Publication Data

US 2022/0313538 A1 Oct. 6, 2022

Related U.S. Application Data

(60) Provisional application No. 63/321,027, filed on Mar. 17, 2022, provisional application No. 63/169,399, filed on Apr. 1, 2021.

(51) Int. Cl.
*A61H 9/00* (2006.01)
*A61H 23/02* (2006.01)
*A61H 39/04* (2006.01)

(52) U.S. Cl.
CPC ........... *A61H 9/0057* (2013.01); *A61H 23/02* (2013.01); *A61H 39/04* (2013.01);
(Continued)

(58) Field of Classification Search
CPC ...... A61H 9/0057; A61H 23/02; A61H 7/008; A61H 7/00; A61H 7/001; A61H 7/007; A61H 9/005; A61H 9/0071; A61H 9/0078
See application file for complete search history.

(56) References Cited

U.S. PATENT DOCUMENTS

| 1,545,027 A | 7/1925 | Ashlock |
| D143,678 S | 1/1946 | Snyder et al. |

(Continued)

FOREIGN PATENT DOCUMENTS

| CN | 201239336 Y | 5/2009 |
| CN | 301664182 S | 9/2011 |

(Continued)

OTHER PUBLICATIONS

Amazon: "Becommend Smart Dynamic Cupping Therapy Set, Cellulite Massager 3 in 1 Vacuum Therapy Machine Cellulite Remover, Gua Sha Massage Tool with 12 Level Temperature and Suction, 12 Level Red," Available at least as early as Jan. 6, 2022, 09 Pages, Retrieved from URL: https://www.amazon.com/Becommend-Dynamic-Cellulite-Massager-Temperature/dp/B09PVF72RJ/ref=sr_1_7keywords=vacuum+cupping&qid=1668816961&sr=8-7.

(Continued)

*Primary Examiner* — Margaret M Luarca
*Assistant Examiner* — Sarah B Lederer
(74) *Attorney, Agent, or Firm* — Sterne, Kessler, Goldstein & Fox P.L.L.C.

(57) ABSTRACT

A suction assembly is described. The suction assembly includes a therapy unit with a body that can apply a supplemental therapy to a skin surface. The suction assembly also includes a cup that can be removably connected to the therapy unit and that can interface with a skin surface to define a chamber within the cup. A pump of the therapy unit can reduce a pressure within the chamber to draw the skin surface into the chamber in a cupping therapy. In response to the skin surface being drawn into the chamber, the body can move in a longitudinal direction to maintain contact with the skin surface. A wall of the cup is translucent and the suction assembly is dimensioned to provide a user with a (Continued)

view into the chamber through the wall of the cup that is substantially unobstructed by the housing.

24 Claims, 10 Drawing Sheets

(52) U.S. Cl.
CPC ................ *A61H 2201/0207* (2013.01); *A61H 2201/1238* (2013.01); *A61H 2201/5025* (2013.01)

(56) References Cited

U.S. PATENT DOCUMENTS

| | | | |
|---|---|---|---|
| 2,987,334 | A | 6/1961 | Wendling |
| 3,705,579 | A | 12/1972 | Morini et al. |
| D230,522 | S | 2/1974 | Rothman |
| 4,046,142 | A | 9/1977 | Whitney |
| 5,103,809 | A | 4/1992 | DeLuca et al. |
| 5,295,982 | A * | 3/1994 | Schatz .................. A61H 9/005 604/315 |
| D439,984 | S | 4/2001 | Thach |
| 6,319,212 | B1 * | 11/2001 | Muller .................. A61H 9/005 601/126 |
| 6,823,762 | B2 | 11/2004 | Hu |
| 7,431,706 | B2 | 10/2008 | Louis |
| 7,927,259 | B1 | 4/2011 | Rix |
| 7,927,294 | B2 | 4/2011 | Kamimura et al. |
| D659,644 | S | 5/2012 | Gretz |
| 8,777,881 | B2 | 7/2014 | Tsai |
| D756,180 | S | 5/2016 | Chen |
| D762,871 | S | 8/2016 | Gomez |
| 9,889,066 | B2 | 2/2018 | Danby et al. |
| D817,732 | S | 5/2018 | Rettler |
| D837,395 | S | 1/2019 | Gan |
| D875,962 | S | 2/2020 | Spratt |
| D888,979 | S | 6/2020 | Chernyavskiy et al. |
| D893,037 | S | 8/2020 | Chernyavskiy et al. |
| D893,038 | S | 8/2020 | Chernyavskiy et al. |
| D907,787 | S | 1/2021 | Chernyavskiy et al. |
| 10,918,859 | B2 * | 2/2021 | Kang ..................... A61N 1/06 |
| D938,601 | S | 12/2021 | Chernyavskiy et al. |
| 2003/0158505 | A1 * | 8/2003 | Calvert ................. A61H 7/005 601/134 |
| 2009/0264971 | A1 * | 10/2009 | Wickstead ................ A61F 7/03 607/108 |
| 2013/0073017 | A1 * | 3/2013 | Liu ........................ A61H 39/06 607/112 |
| 2015/0231021 | A1 * | 8/2015 | Smith ..................... A61M 1/90 601/7 |
| 2016/0367425 | A1 | 12/2016 | Wersland |
| 2017/0042754 | A1 | 2/2017 | Fowers et al. |
| 2017/0197016 | A1 | 7/2017 | Palomäki et al. |
| 2017/0252261 | A1 * | 9/2017 | Khorassani Zadeh ...................... A61H 9/0057 |
| 2017/0290732 | A1 * | 10/2017 | Palomäki ................. A61H 9/00 |
| 2017/0304145 | A1 | 10/2017 | Pepe |
| 2018/0141188 | A1 | 5/2018 | Lai |
| 2018/0168915 | A1 | 6/2018 | Gwen |
| 2020/0179220 | A1 * | 6/2020 | Jablow ..................... A61H 1/00 |
| 2020/0222269 | A1 * | 7/2020 | Rodan ..................... A61K 8/37 |
| 2021/0330539 | A1 | 10/2021 | Faussett |
| 2022/0062093 | A1 * | 3/2022 | Blanche ................. A61N 7/00 |
| 2022/0096312 | A1 * | 3/2022 | Liu ........................ A61H 23/00 |

FOREIGN PATENT DOCUMENTS

| | | | |
|---|---|---|---|
| CN | 202637439 | U | 1/2013 |
| CN | 303250924 | S | 6/2015 |
| CN | 303250929 | S | 6/2015 |
| CN | 303389903 | | 9/2015 |
| CN | 106859949 | A | 6/2017 |
| CN | 304402478 | | 12/2017 |
| CN | 304561844 | S | 3/2018 |
| CN | 207855923 | U | 9/2018 |
| CN | 109528473 | A | 3/2019 |
| CN | 305204757 | | 6/2019 |
| CN | 305318195 | | 8/2019 |
| CN | 305651009 | | 3/2020 |
| CN | 305934474 | | 7/2020 |
| CN | 306270046 | | 1/2021 |
| CN | 306394753 | | 3/2021 |
| CN | 306707158 | | 7/2021 |
| CN | 306804037 | | 9/2021 |
| CN | 306995184 | | 12/2021 |
| CN | 307627107 | | 10/2022 |
| CN | 307654068 | | 11/2022 |
| JP | S5428491 | A | 3/1979 |
| JP | H0447440 | U | 4/1992 |
| JP | 2000189525 | A | 7/2000 |
| JP | 2011502369 | A | 1/2011 |
| JP | 5129032 | B2 | 1/2013 |
| JP | 2014511240 | A | 5/2014 |
| KR | 20030056370 | A | 7/2003 |
| KR | 101162978 | B1 | 7/2012 |
| KR | 20170108550 | A | 9/2017 |
| TW | I359657 | B | 3/2012 |
| WO | WO-2021092586 | A1 * | 5/2021 ............... A61H 1/00 |

OTHER PUBLICATIONS

Amazon: "Therabody TheraCup," Accessed on Jan. 25, 2023, 2 Pages, Retrieved from URL: https://www.amazon.com/stores/Theragun/TheraCup/page/D78B5C29-E218-4C0E-80DC-B9A59ADE066B.

Anthony Katz, "The Raptor: Helps Patients and Saves Your Most Valuable Tool . . . Your Hands," DC Aligned:MeyerDC, Dec. 9, 2015, available at: http://news.meyerdc.com/community/vendor-spotlight/the-raptor-helps-patients-saves-your-most-valuable-tool-your-hands/ (last visited Feb. 15, 2023); 5 pages.

Defendant's Initial Invalidity Contentions, *Therabody, Inc.* v. *Tzumi Electronics LLC et al.*, Case No. SDNY-1-21-cv-07803 (PGG)(RWL), dated Aug. 17, 2022; 16 pages.

Description of Therabody GI Device, available at: https://www.therabody.com/us/en-us/faq/thearagun-devices/faq-devices-1.html?fdid=faq&csortb1=sortOrder&csortd1=1 (last visited Feb. 15, 2023).

Holly Riddle, "Theragun vs. Hyperice vs, Hydragun: Massage Gun Showdown [Buyer's Guide]," ChatterSource: Health & Wellness, Mar. 9, 2021, available at: https://www.chattersource.com/article/massage-gun/ (last visited Feb. 17, 2023); 14 pages.

International Search Report and Written Opinion for International Application No. PCT/US2022/023100, dated Aug. 29, 2022, 17 Pages.

Therabody: "TheraCup," Accessed on Jan. 25, 2023, 01 Page, Retrieved from URL: https://www.therabody.com/us/en-us/theracup-cupping-therapy.html.

Visual Description of Hyper Ice, Inc. Raptor Device, "Osteopatia Haidy Ortale—Raptor Massage," available at: https://www.youtube.com/watch?v=plyW8FBowVs (last visited Feb. 15, 2023); 1 page.

Visual Description of Hyper Ice, Inc. Raptor Device, "Raptor Solutions 1.3 Prone," available at: https://www.youtube.com/watch?v=6i1tRqdwPU8&t=156s (last visited Feb. 15, 2023); 1 page.

Youtube: "First Look: Therabody TheraCup—Can It Do Gliding Cupping?," Published Date on Dec. 1, 2022, 01 Page, Retrieved from URL: https://www.youtube.com/watch?v=yP0S5N24GMk.

* cited by examiner

SUCTION ASSEMBLY

CROSS REFERENCE TO RELATED APPLICATIONS

This application claims the benefit of U.S. Provisional Patent App. No. 63/169,399, filed Apr. 1, 2021, and U.S. Provisional Patent App. No. 63/321,027, filed Mar. 17, 2022, the disclosures of which are hereby incorporated by reference herein.

TECHNICAL FIELD

This application generally relates to suction assemblies, and particularly suction assemblies that can perform cupping therapy alone or together with other supplemental therapies.

BACKGROUND

Cupping therapy is treatment that involves applying suction to a local area of the skin. Cupping therapy may be effective for treating a wide array of medical conditions including muscle pain, high blood pressure acne, psoriasis, infertility, among others. Traditional cupping techniques include dry cupping and fire cupping. Dry cupping can involve heating a cup with the open end applied to a skin surface. As the cup cools the pressure within the cup can decrease, which can create the suction effect of the cupping therapy. Fire cupping can involve igniting a combustible material and quickly placing the ignited material within the cup and then placing the cup against the skin surface. The ignited material then consumes the oxygen within the cup causing the pressure to decrease, which can create the suction effect of the cupping therapy. These traditional cupping techniques can be dangerous and unhygienic. For example, the poorly regulated heating of the dry cupping and burning of the combustible material can burn the skin surface. Further, it is difficult to control the pressure within the cups using these traditional cupping techniques. Traditional cupping techniques are best performed by trained practitioners, which can limit widespread use of cupping therapies.

Accordingly, there exists a need for a suction assembly that can reliably perform cupping therapy alone or together with other therapies, that can be used easily and safely by inexperienced users without the supervision of trained practitioners, and that can regulate the cupping therapy and/or other therapies to eliminate or reduce adverse effects of the cupping therapy.

SUMMARY

These needs are met, to a great extent, by a suction assembly that includes a therapy unit. The therapy unit includes: a housing extending along a longitudinal direction, an inlet provided at a first end of the housing, an outlet provided at a second end of the housing, a pump in fluid communication with the inlet and the outlet, and a body provided at the first end of the housing and that is configured to apply a supplemental therapy to a skin surface. The assembly also includes a cup that defines a first opening and a second opening. The first opening is configured to be removably connected to an intermediate portion of the housing and the second opening is configured to interface with the skin surface to define a chamber within the cup. The body of the therapy unit is movable in the longitudinal direction. The pump is configured to reduce a pressure within the chamber to draw the skin surface into the chamber by pumping gas from the chamber into the inlets and exhausting the gas out the outlets. In response to the skin surface being drawn into the chamber the body moves in the longitudinal direction to maintain contact with the skin surface.

Implementations may include one or more of the following features. The suction assembly where the cup is a first cup and the chamber is a first chamber, and the suction assembly further may include a second cup that is interchangeable with the first cup. The second cup defines a first opening and a second opening. The first opening of the second cup is configured to be removably connected to the intermediate portion of the housing and the second opening of the second cup is configured to interface with the skin surface to define a second chamber within the second cup. A volume of the first chamber is different than a volume of the second chamber. A diameter of the second opening of the first cup is different than a diameter of the second opening of the second cup. When the second cup is interchanged with the first cup and the first opening of the second cup is removably connected to the intermediate portion of the housing, the pump is configured to reduce a pressure within the second chamber to draw the skin surface into the second chamber by pumping gas from the second chamber into the inlets and exhausting the gas out the outlets, and where in response to the skin surface being drawn into the second chamber the body moves in the longitudinal direction to maintain contact with the skin surface. The body is movable in the longitudinal direction between an extended position, a retracted position, and an intermediate position between the extended position and the retracted position. The body is biased towards the extended position. The supplemental therapy is heat. The suction assembly may include a controller that is configured to control the heater to heat at a predetermined intensity. The supplemental therapy is vibration. The suction assembly may include a controller that is configured to control the motor at a predetermined intensity. The body includes protrusions and the supplemental therapy is acupressure. The suction assembly may include a filter that is removably and connected between the inlet and the pump. Implementations of the described techniques may include hardware, a method or process, or computer software on a computer-accessible medium.

One general aspect includes a suction assembly that includes a therapy unit. The therapy unit includes: a housing extending along a longitudinal direction; an inlet provided at a first end of the housing; an outlet provided at a second end of the housing; a pump in fluid communication with the inlet and the outlet; and a body provided at the first end of the housing that is configured to apply a supplemental therapy to a skin surface. The assembly also includes a cup that defines a first opening, a second opening, and a wall between the first opening and the second opening. The first opening is configured to be removably connected to an intermediate portion of the housing and the second opening is configured to interface with the skin surface to define a chamber within the cup. The pump is configured to reduce a pressure within the chamber and to draw the skin surface into the chamber by pumping gas from the chamber into the inlets and exhausting the gas out the outlets. The wall of the cup is translucent and the suction assembly is dimensioned to provide a user with a view into the chamber through the wall of the cup that is substantially unobstructed by the housing.

Implementations may include one or more of the following features. The suction assembly is dimensioned such that a width of the cup at the second opening is within a range of plus or minus fifteen percent of a maximum width of the housing to provide the user with the view into the chamber through the wall of the cup that is substantially unobstructed by the housing. The suction assembly is dimensioned such that a maximum height of the suction assembly is between 1.5 and 1.75 times larger than a maximum width of the housing to provide the user with the view into the chamber through the wall of the cup that is substantially unobstructed by the housing. The therapy unit further may include a plurality of rings at the intermediate portion of the housing that together with the first opening of the cup define a pressure-tight connection between the intermediate portion of the housing and the cup. The suction assembly may include a controller that is configured to control a function of the therapy unit in response to a command received from an external device. The external device is a second suction assembly. The cup is a first cup and the chamber is a first chamber, and the suction assembly further may include a second cup that is interchangeable with the first cup. The second cup defines a first opening and a second opening, the first opening of the second cup is configured to be removably connected to the intermediate portion of the housing and the second opening of the second cup is configured to interface with the skin surface to define a second chamber withing the second cup. A volume of the first chamber is different than a volume of the second chamber. A diameter of the second opening of the first cup is different than a diameter of the second opening of the second cup. Implementations of the described techniques may include hardware, a method or process, or computer software on a computer-accessible medium.

Various additional features and advantages of this invention will become apparent to those of ordinary skill in the art upon review of the following detailed description of the illustrative embodiments taken in conjunction with the accompanying drawings.

BRIEF DESCRIPTION OF THE DRAWINGS

The following detailed description is better understood when read in conjunction with the appended drawings. For the purposes of illustration, examples are shown in the drawings; however, the subject matter is not limited to the specific elements and instrumentalities disclosed. In the drawings.

DETAILED DESCRIPTION OF ILLUSTRATIVE EMBODIMENTS

Figure 1:
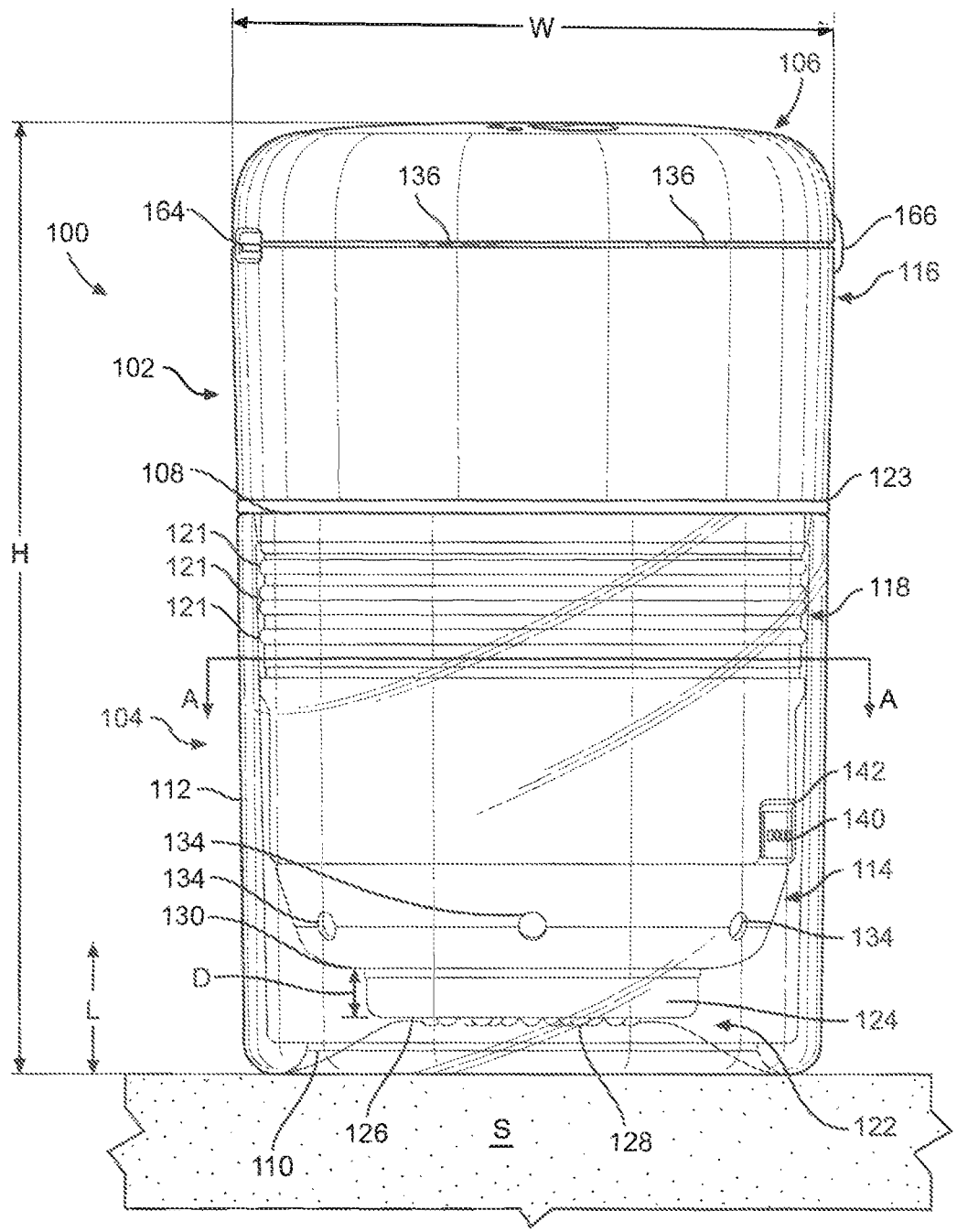
FIG. 1 shows a side view of a suction assembly with a body provided in an extended position.
Figure 2:
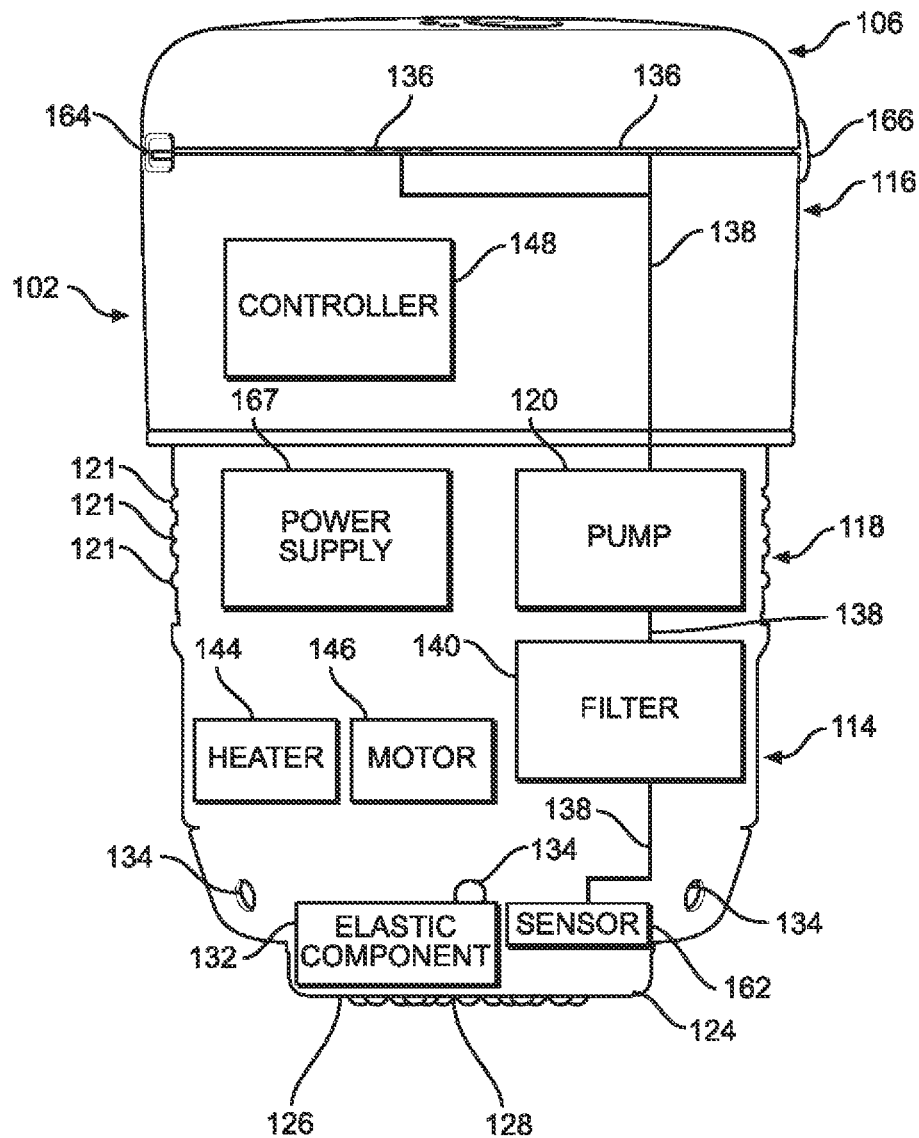
FIG. 2 shows a schematic view of a therapy unit of the suction assembly of FIG. 1.

FIGS. 1-10 show aspects of a suction assembly 100 that includes a therapy unit 102 and a cup 104 in accordance with aspects of this disclosure. The cup 104 can include a first opening 108, a second opening 110, and a wall 112 extending between the first opening 108 and the second opening 110. The therapy unit 102 can include a housing 106 that can house components of the therapy unit 102. The housing 106 can include a first end 114, a second end 116, and an intermediate portion 118 extending between the first end 114 and the second end 116. The therapy unit 102 can also include a pump 120, as shown in FIG. 2. The first opening 108 of the cup 104 can be removably connected to the intermediate portion 118 of the housing 106. For example, the intermediate portion 118 of the housing 106 can include one or more resilient, circumferential rings 121 that can form a removable, pressure-tight connection between the intermediate portion 118 of the housing and the cup 104. The rings 121 can be dimensioned relative to the first opening 108 of the cup 104 such that the pressure-tight connection between the intermediate portion 118 is formed when a user both pushes the first opening 108 and the cup 104 together in the longitudinal direction L and also twists the cup 104 and the therapy unit 102 together. The rings 121 can be dimensioned relative to the first opening 108 of the cup 104 such that the pressure-tight connection between the intermediate portion 118 is formed when a user either pushes the first opening 108 and the cup 104 together in the longitudinal direction L or twists the cup 104 and the therapy unit 102 together. In embodiments, the intermediate portion 118 can include three circumferential rings 121, though other numbers of rings 121 are possible including only a single ring 121. Additionally or alternatively, the intermediate portion 118 can include a protection ring 123. The protection ring 123 can project radially outward beyond the cup 104 in directions perpendicular to the longitudinal direction L of the therapy unit 102. The protection ring 123 can completely or partially surround the therapy unit 102. The protection ring 123 can be disposed at the interface between the first opening 108 of the cup 104 and the therapy unit 102. The protection ring 123 can include a resilient material such as rubber or the like. According to these features, the protection 123 can absorb impact forces when the suction assembly 100 is dropped and protect the cup 104 and/or the therapy unit 102 from being damaged.

The second opening 110 of the cup 104 can interface with a skin surface S to define a chamber 122 within the cup 104. The pump 120 can reduce pressure within the chamber 122 to draw the skin surface S into the chamber 122. The reduction of pressure within the chamber 122 to draw the skin surface S into the chamber can be referred to herein as a "cupping therapy." The cupping therapy can be administered by the suction assembly 100 with our without lotion and/or oil provided on the skin surface S.

The therapy unit 102 can also include a body 124 that can apply a supplemental therapy to the skin surface S. The term "supplemental therapy" as used herein can refer to therapies applied to the skin surface S by the body 124 and can include, for example, heat therapy, vibration therapy, acupressure, among others. Accordingly, the therapy unit 102 As shown particularly in the bottom view of FIG. 7, the body 124 can include a contact surface 126 that can directly contact the skin surface S when the skin surface S is drawn into the chamber 122. In embodiments, the body 124 and/or contact surface 126 can include a material with a high thermal conductivity such as steel or copper that can efficiently transfer heat from a heater 144 to the skin surface S. In embodiments, the contact surface 126 can be a removable cap. In embodiments, the contact surface 126 can include a galvanized coating. In embodiments, the contact surface 126 can include painted steel. In embodiments, the heater 144 can be a heating ring. In embodiments, the contact surface 126 can have a diameter between 30 and 38 mm, such as for example 34 mm. In embodiments, the contact surface 126 can have a thickness of approximately 0.5 mm+/−10%, which can improve heat transfer between the heater 144 and the skin surface S. In embodiments, the contact surface 126 can include protrusions 128. Alternatively, the contact surface 126 can be provided without protrusions 128 and can be substantially flat. In response to the skin surface S being drawn into the chamber 122 during the cupping therapy the body 124 can move in a longitudinal direction L to maintain contact with and/or conform to the skin surface S. This can allow varying intensities of cupping therapy to be performed on the skin surface without compromising the efficacy of the supplemental therapy since the body 124 can maintain a consistent, even contact with the skin surface S during the supplemental therapy even as different amounts of skin is drawn into the chamber 122 in response to varying intensities of cupping therapy. The body 124 can move or travel a distance D in the longitudinal direction L. In embodiments, the distance D can be between 9 mm and 12 mm such as for example 10.5 mm. In embodiments, the distance D can be up to 20 mm.

FIG. 1 shows the application of a first magnitude of cupping therapy in which the pump 120 reduces the pressure within the chamber 122 to draw the skin surface into the chamber 122. The first magnitude can be moderate such that the skin surface S contacts with the contact surface 126 of the body 124 without moving the body 124 in the longitudinal L. The body 124 can be positioned in an extended position, as shown in FIG. 1, at which the contact surface 126 of the body 124 is disposed the distance D away from a bottom 130 of the first end 114 of the housing 106. The body 124 can be biased towards the extended position via a resilient component 132. The resilient component 132 can for example be a spring or functionally equivalent structure. The body 124 can remain in the extended position until the biasing force is overcome for example by skin drawn into the chamber 122.

Figure 3:
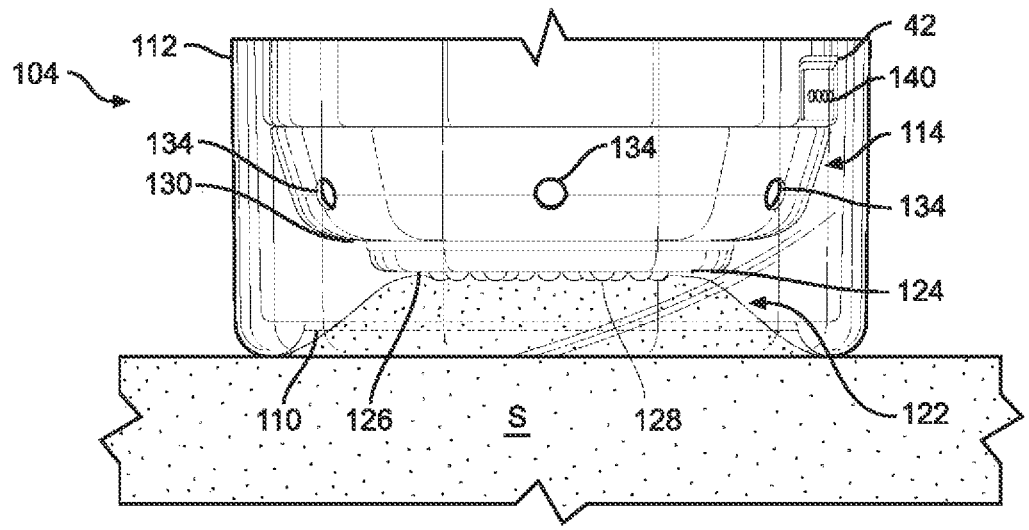
FIG. 3 shows a side view of a portion of the suction assembly of FIG. 1 with the body provided in an intermediate position.
Figure 4:
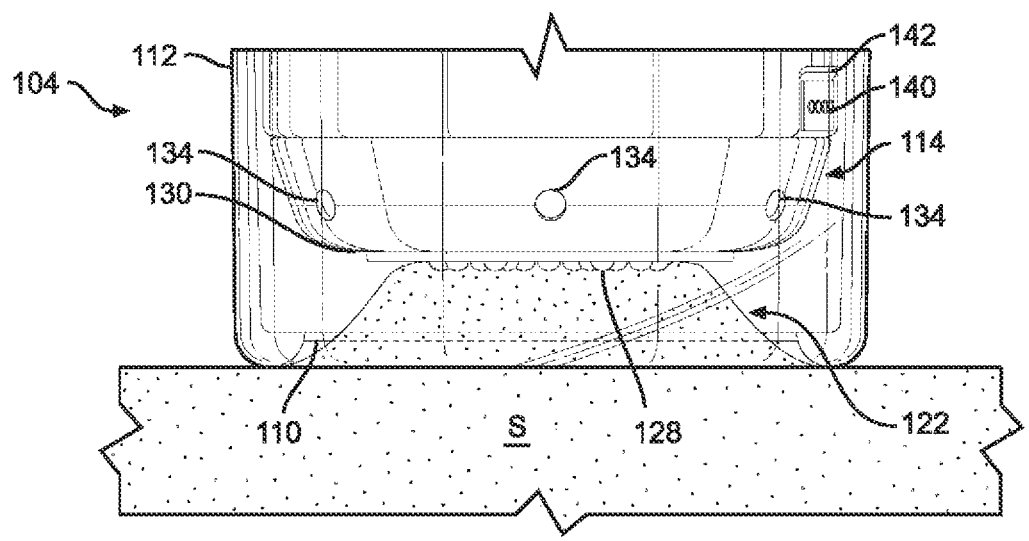
FIG. 4 shows a side view of a portion of the suction assembly of FIG. 1 with the body provided in a retracted position.

FIGS. 3 and 4 show partial views of the suction assembly 100 of FIG. 1 during application of magnitudes of cupping therapy greater than the first magnitude. For example, FIG. 3 shows the application of a second magnitude of cupping therapy in which the pump 120 further reduces the pressure within the chamber 122 to draw more skin into the chamber 122. The second magnitude of cupping therapy can be greater than the first magnitude of cupping therapy. The additional skin drawn into the chamber 122 as a result of the application of the second magnitude of cupping therapy can move the body 124 in the longitudinal direction L and the body 124 can retract into the first end 114 of the housing 106 to an intermediate position.

FIG. 4 shows the application of a third magnitude of cupping therapy in which the pump 120 still further reduces the pressure within the chamber 122 to draw even more skin into the chamber 122. The third magnitude of cupping therapy can be greater than both the first and the second magnitudes of cupping therapy. The additional skin drawn into the chamber 122 as a result of the application of the third magnitude of cupping therapy can further move the body 124 in the longitudinal direction L and further retract the body 124 into the first end 114 of the housing 106 to a retracted position. At the retracted position, the contact surface 126 can be disposed the distance D towards the first end 114 of the housing 106 relative to the extended position and the contact surface 126 can be substantially flush with the bottom 130 of the first end 114 of the housing 106. The intermediate position shown in FIG. 3 can be any position between the extended position and the retracted position.

Returning to FIG. 1, a wall 112 of the cup 104 can be translucent and the suction assembly 100 can be dimensioned so as to provide a user views into the chamber 122 that are substantially unobstructed by the housing 106. The views substantially unobstructed by the housing 106 can be from vantage points that are offset from the direct top-down view of the second end 116 of the housing 106 shown in FIG. 6. According to this arrangement, the user can more easily monitor the skin surface S undergoing the cupping and/or supplemental treatment. User monitoring of the skin surface S undergoing the cupping and/or supplemental treatment can improve the safety and usability of the device by for example allowing adverse reactions to be detected and by providing an opportunity for the user to discontinue treatment in response to the adverse reactions.

Figure 5:
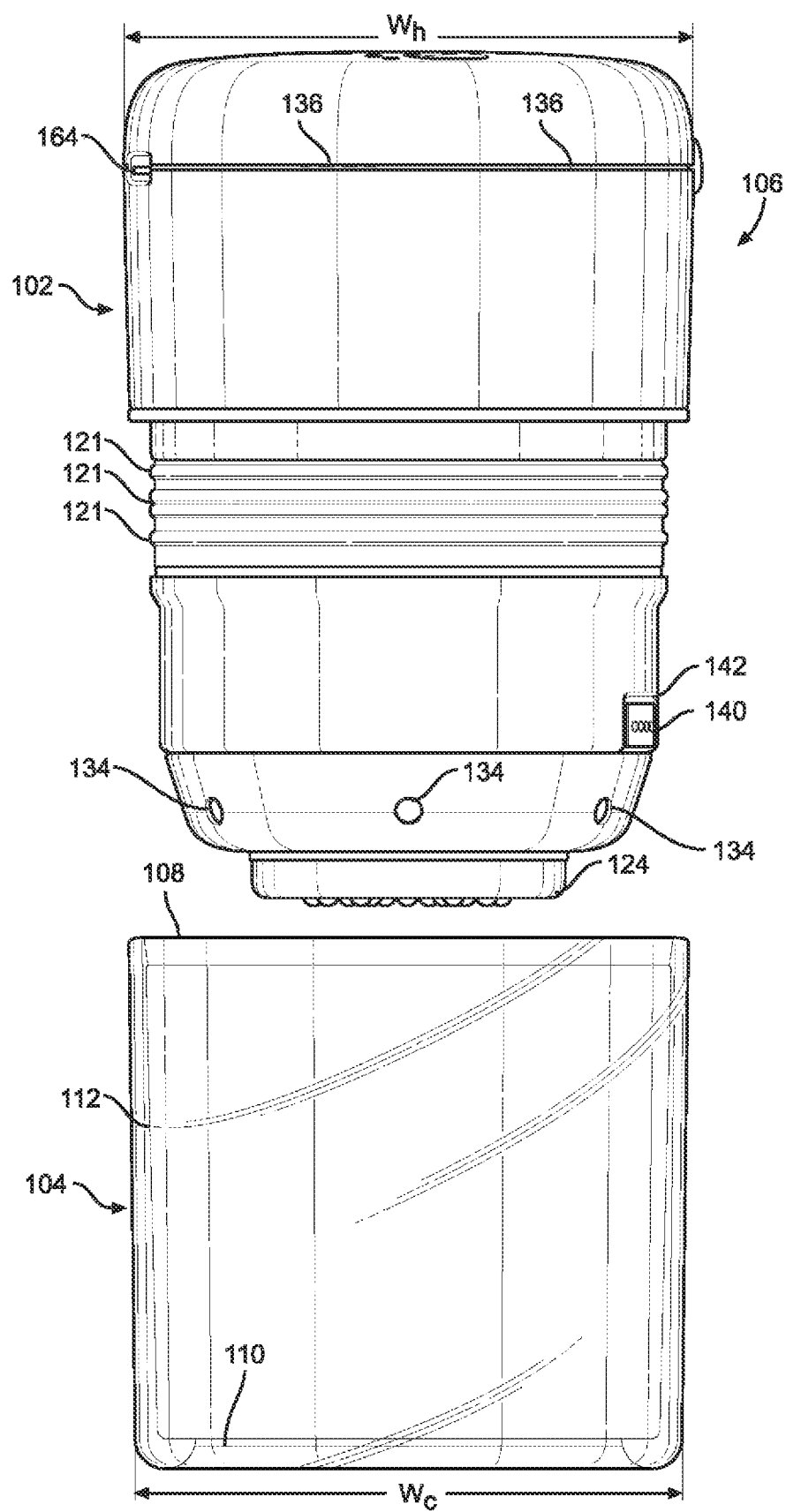
FIG. 5 shows an exploded side view of the suction assembly of FIG. 1.

The suction assembly 100 can be dimensioned in a number of ways to provide the user with the views into the chamber 122 that are substantially unobstructed by the housing 106. For example, as shown in FIG. 5 a width $W_c$ of the cup 104 at the second opening 110 can be similar to, that is within a range of +/−15%, of a maximum width $W_h$ of the housing 106. According to this arrangement, the housing 106 does not substantially project outwardly beyond the second opening 110 of the cup 104 and thus the housing 106 does not substantially obstruct views through the translucent cup 104 into the chamber 122.

Additionally or alternatively, a maximum height H of the assembled suction assembly 100 can be at least 1.3 times larger than a maximum width W of the assembled suction assembly 100, as shown in FIG. 1. In embodiments, the maximum height H can be between 1.3 and 1.8 times larger than the maximum width W. In embodiments, the maximum height H can be between 1.5 times and 1.75 times larger than the maximum width W. According to these aspects, components of the therapy unit 102 can be arranged compactly within the housing 106 along the longitudinal direction L and the therapy unit 102 can have an elongated form factor that does not substantially obstruct views into the chamber 122 through the cup 104. Further, this arrangement allows the suction assembly 100 to have a center of gravity low enough to stably balance the suction assembly 100 on a user when the pump 120 pumps skin into the chamber 122. This can allow users to administer the cupping and/or supplemental therapies without the need to stabilize the device and thereby improving the usability of the suction assembly 100.

As shown in FIGS. 1 and 2 and as discussed previously, the therapy unit 102 can include the pump 120 that can reduce pressure within the chamber 122 to draw skin into the chamber 122 during the cupping therapy. The pump 120 can be fluidly connected to inlets 134 that can be provided at the first end 114 of the housing 106 within the chamber 122. The pump 120 can be fluidly connected to outlets 136 that can be provided at the second end 116 of the housing 106 outside of the chamber 122. The pump 120 can reduce pressure within the chamber 122 by drawing gas from within the chamber 122 into inlets 134 and exhausting the gas out of the outlets 136. Therapy unit 102 can include a fluid pathway 138 that can include pipes, conduits, ducts, or the like. Fluid pathway 138 can fluidly connect the pump 120, the inlets 134, and the outlets 136. In embodiments, the therapy unit 102 can include a filter 140. The filter 140 can be disposed in the fluid pathway 138 between the inlets 134 and the pump 120. The filter 140 can filter particulates, debris, and the like from gas entering the pump 120, which can extend the life of the pump 120. The filter 140 can be replaceable. For example, as shown in FIG. 1 the housing 106 can include an opening 142 that can removably accommodate the filter 140.

As discussed above, the therapy unit 102 can also include the body 124 that can apply supplemental therapy to the skin surface S. The supplemental therapy can include heat therapy, vibration therapy, acupressure, among others. In embodiments, the therapy unit 102 can include a heater 144 that can be operatively connected to the body 124. The heater 144 can heat the body 124 including the contact surface 126 such that the contact surface 126 can administer heat therapy to the skin surface S. Additionally or alternatively, the therapy unit 102 can include a motor 146 that can be operatively coupled to the body 124. In embodiments, the motor 146 can be surrounded with a noise reducing material such as a foam to reduce noise generated by the motor 146. The motor 146 can vibrate the body 124 including the contact surface 126 such that the contact surface 126 can administer vibration therapy to the skin surface S. In embodiments, the motor 146 can vibrate the contact surface 126 at a frequency between 20 and 40 Hz. The motor 146 can be a vibrating motor, which can be pill or coin shaped among other possibilities. As discussed previously, the contact surface 126 can include protrusions 128. Since the body 124 can be biased, for example via the resilient component 132, towards the extended position protrusions 128 can administer acupressure therapy as the skin is drawn into the chamber 122 and counters the biasing force during the cupping therapy.

The therapy unit 102 can include a controller 148 that can be operatively connected to components of the therapy unit 102 and can control operation of such components. Controller 148 can include for example a processor and a non-transitory computer readable medium such as a memory that can contain instructions executable by the processor for controlling various components of the therapy unit 102.

Figure 6:
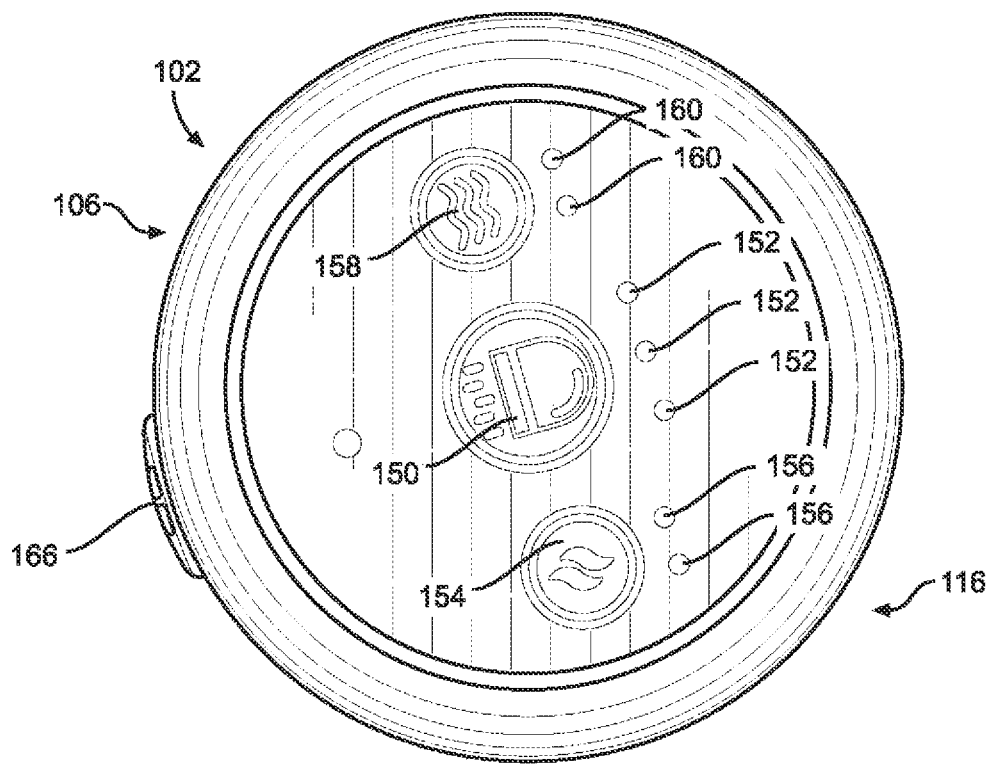
FIG. 6 shows a top view of the therapy unit of FIG. 1.
Figure 7:
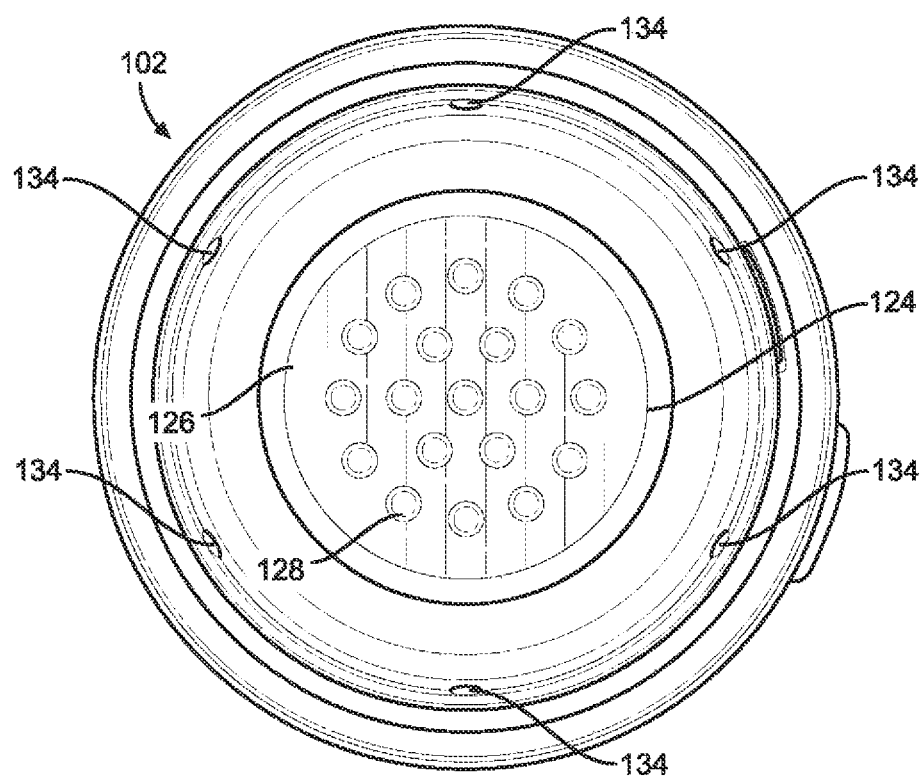
FIG. 7 shows a bottom view of the therapy unit of FIG. 1.

In embodiments, the controller 148 can be operatively coupled to the pump 120 and can control for example pumping intensity and/or duration. In embodiments, the controller 148 can control the pump 120. For example, the controller 148 can control the pumping of the pump 120 at predetermined pumping intensities. As shown in FIG. 6, the therapy unit 102 can include a first button 150 at the second end 116 of the housing 106. The first button 150 can be operatively connected to the controller 148 to allow a user to control the pump 120. For example, pressing the first button 150 once can turn the pump 120 on and initiate pumping at a first intensity to administer the first magnitude of cupping therapy. Pressing the first button 150 a second time can increase intensity of the pumping to a second intensity greater than the first intensity to administer the second magnitude of cupping therapy. Pressing the first button 150 a third time can increase intensity of the pumping to a third intensity greater than both the first and the second intensity to administer the third magnitude of cupping therapy. Pressing the first button 150 a fourth time can turn off the pump 120 to discontinue the cupping therapy. More or less than three predetermined intensities can be controlled by controller 148. Therapy unit 102 can include first indicators 152 at the second end 116 of the housing 106 proximal to the first button 150 to indicate pumping intensity. The first indicators 152 can be visual indicators such as for example lights, audio indicators such as speakers, and/or haptic indicators that provide intensity indication via vibrating motors.

In embodiments, controller 148 can be operatively coupled to heater 144 and can control for example heating intensity and/or duration. In embodiments, controller 148 can control the heater 144 to heat the body 124 at predetermined intensities. As shown in FIG. 6, the therapy unit 102 can include a second button 154 at the second end 116 of the housing 106. The second button 154 can be operatively connected to the controller 148 to allow a user to control the heater 144. For example, pressing the second button 154 once can turn the heater 144 on and initiate heating at a first intensity to administer a first magnitude of heat therapy. Pressing the second button 154 a second time can increase intensity of the heating to a second intensity greater than the first intensity to administer a second magnitude of heat therapy. Pressing the second button 154 a third time can turn off the heater 144 to discontinue the heat therapy. More or less than two predetermined intensities can be controlled by controller 148. Therapy unit 102 can include second indicators 156 at the second end 116 of the housing 106 proximal to the second button 154 to indicate heating intensity. The second indicators 156 can be visual indicators such as for example lights, audio indicators such as speakers, and/or haptic indicators that provide intensity indication via vibrating motors.

In embodiments, controller 148 can be operatively coupled to the motor 146 and can control for example vibration intensity and/or duration. In embodiments, controller 148 can control the motor 146 to vibrate the body 124 at predetermined intensities. As shown in FIG. 6, the therapy unit 102 can include a third button 158 at the second end 116 of the housing 106. The third button 158 can be operatively connected to the controller 148 to allow a user to control the motor 146. For example, pressing the third button 158 once can turn the motor 146 on and initiate vibrating at a first intensity to administer a first magnitude of vibration therapy. Pressing the third button 158 a second time can increase intensity of the vibrating to a second intensity greater than the first intensity to administer a second magnitude of vibration therapy. Pressing the third button 158 a third time can turn off the motor 146 to discontinue the vibration therapy. More or less than two predetermined intensities can be controlled by controller 148. Therapy unit 102 can include third indicators 160 at the second end 116 of the housing 106 proximal to the third button 158 to indicate vibration intensity. The third indicators 160 can be visual indicators such as for example lights, audio indicators such as speakers, and/or haptic indicators that provide intensity indication via vibrating motors.

In any of the above described embodiments, controller 148 can include safety features such as an automatic shut off that can discontinue therapies controlled by controller 148. For example, controller 148 can automatically shut off the pump 120, the heater 144, and/or the motor 146 to discontinue a therapy after a predetermined period of time such as for example 3 minutes. This safety feature can improve the usability of the suction assembly 100 and allow inexperienced users to administer therapies with limited risk of adverse effects.

Returning to FIG. 2, the therapy unit 102 can include one or more sensors 162 that can sense conditions associated with the cupping therapy, supplemental therapies, and/or operation of the therapy unit 102. Sensors 162 can be operatively coupled to controller 148 and controller 148 can utilize conditions sensed by sensors 162 to control operation of various components of the therapy unit 102. For example, sensor 162 can be a pressure sensor that can sense a pressure within the chamber 122 and the controller 148 can use the pressure sensed by the sensor 162 to control operation of the pump 120. Additionally or alternatively, sensor 162 can include a temperature sensor that can sense the temperature within the chamber 122 and/or of the body 124 and the controller 148 can use the temperature sensed by the sensor 162 to control operation of the heater 144. Additionally or alternatively, sensor 162 can include a proximity sensor that can sense conditions associated with skin deformation.

Figure 8:
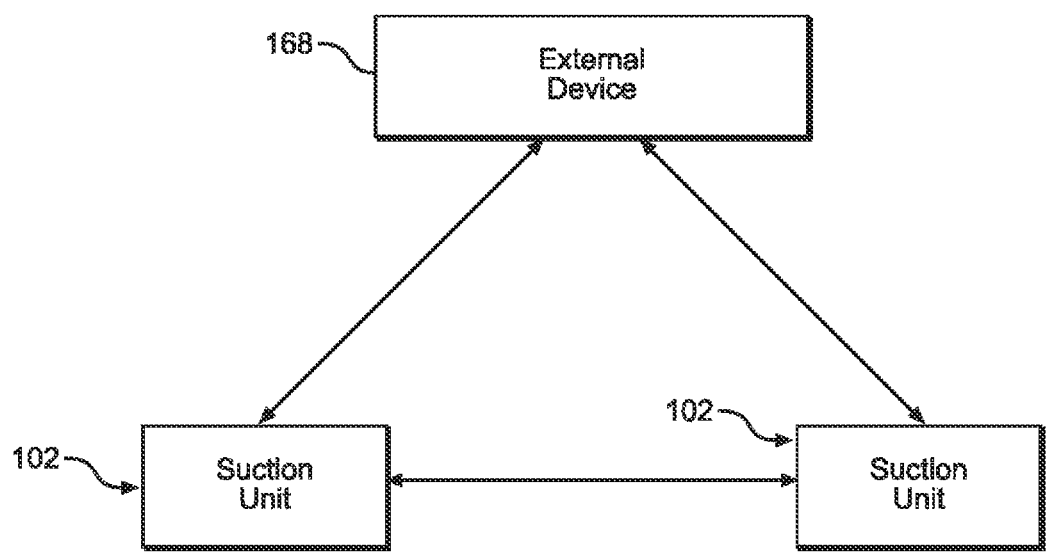
FIG. 8 shows a schematic therapy unit network arrangement.

Controller 148 can internally utilize the data collected by sensor 162 and/or, as shown in FIG. 8, the controller 148 can transmit data collected by the sensor 162 to an external device 168, such as for example a smartphone (or the like) or another therapy unit 102. That is, controller 148 can include a transmitter and a receiver for communicating externally. Controller 148 can wirelessly transmit/receive data to and/or from other devices using the transmitter and the receiver using for example Bluetooth protocols. Controller 148 can communicate with an application on a remote electronic device, such as a server, a smartphone, tablet, or laptop. A user may select the therapy using the application. The application may suggest different predefined therapies depending on the muscle group that the cups are applied to.

Additionally or alternatively therapy unit 102 can include an input/output 164 that can reciprocally transmit data or that can be used to power or charge therapy unit 102. Therapy unit 102 can include a power supply 167 such as a battery or functional equivalent that can power pump 120, heater 144, motor 146, controller 148, sensor 162, etc. Therapy unit 102 can include an on-off switch 166 the can turn the therapy unit 102 on and off. This can, for example, allow a user to immediately discontinue any therapy controlled by the therapy unit 102 by switching off the on-off switch 166. In embodiments, therapy unit 102 can include one or more far infrared LED lights for supplemental treatments. Alternatively, therapy unit 102 can be provided without far infrared LED lights to simplify the therapy unit 102.

As shown schematically in FIG. 8, the therapy unit 102 can be networked with any number of other therapy units 102 and/or with another external device 168, such as a smartphone, for transmitting data between therapy units 102 and/or external device 168. For example, external device 168 can send signals to one or more therapy units 102 to control for example cupping therapy and/or supplemental therapies administered by the therapy units 102. Additionally or alternatively, one therapy unit 102 can be paired with any number of other therapy units 102 and control commands can be sent from one therapy unit 102 to the other therapy unit(s) 102 such that all therapy units 102 perform the same therapies. For example, pressing the first button 150 on one therapy unit 102 to initiate a first magnitude of cupping therapy can automatically trigger initiation of a first magnitude of cupping therapy on the other therapy unit 102 via the paired connection. Any number of therapy units 102 and therapies can be controlled by a single therapy unit 102 in a similar manner. This can be particularly useful for treating large areas of the body such as the back.

Figure 9:
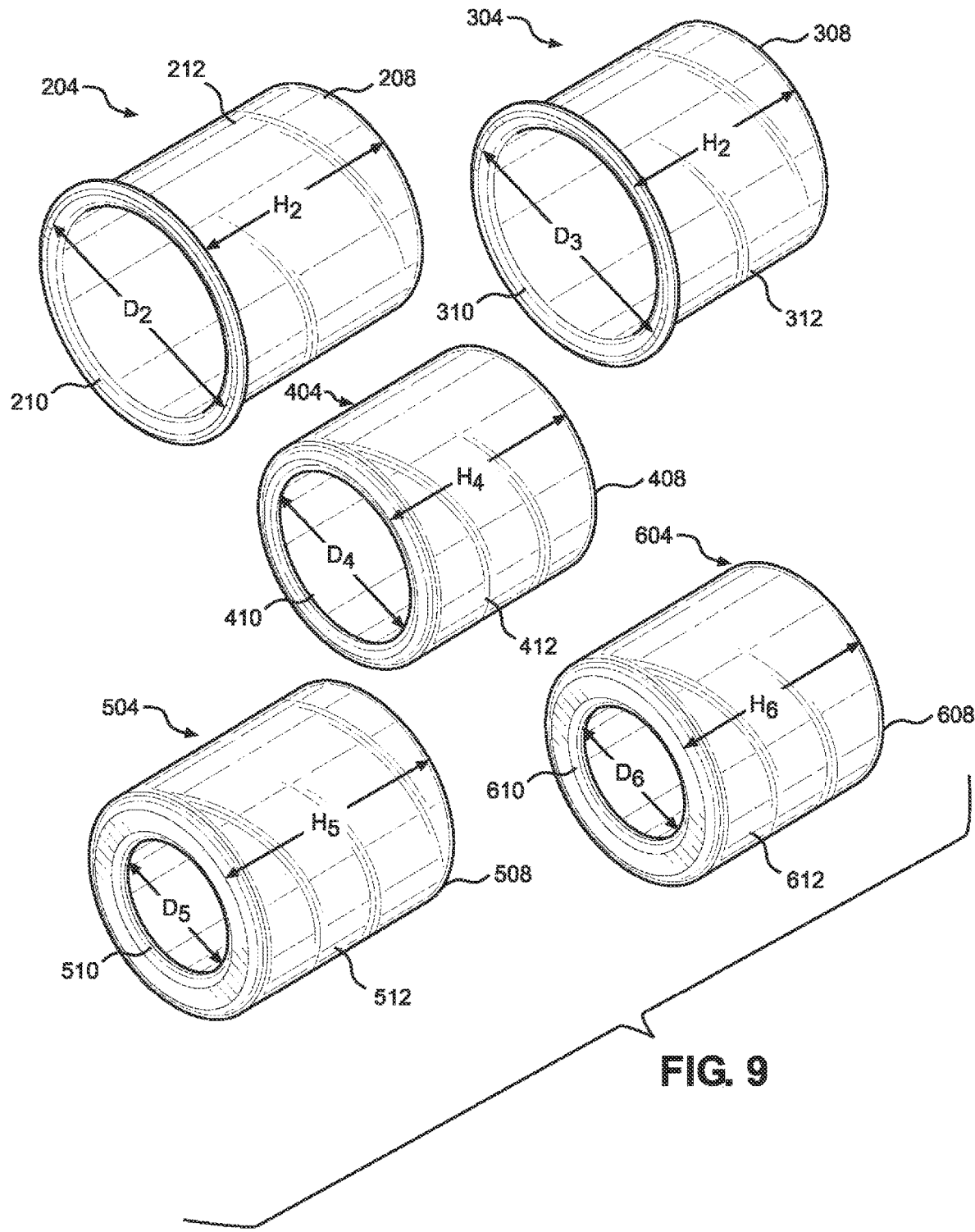
FIG. 9 shows a plurality of different interchangeable cups of the suction.

Referring to FIG. 9, the suction assembly 100 can be provided in a kit where a therapy unit 102 comes with a plurality of interchangeable cups 204, 304, 404, 504, 604. Cups 204, 304, 404, 504, 604 can include any of the features discussed previously in reference to cup 104 and can interface with the therapy unit 102 and the skin surface S in similar manners. For example, each of the cups 204, 304, 404, 504, 604 can include a respective first opening 208, 308, 408, 508, 608 for removably connecting to the intermediate portion 118, as discussed previously. Each of the cups 204, 304, 404, 504, 604 can include a respective a second opening 210, 310, 410, 510, 610 for interfacing with a skin surface S to define a respective chamber (not shown) within the respective cup 204, 304, 404, 504, 604, as discussed previously. That is, a first chamber may be defined when a first cup 204 is connected to the therapy unit 102 and when the second opening 210 of the first cup 204 interfaces with the skin surface S. A second chamber may be defined when a second cup 304 is interchanged with the first cup 204 and the second cup 304 is connected to therapy unit 102 in a similar manner, and so on and so forth for each of third, fourth, and fifth cups 404, 504, 605. Respective walls 212, 312, 412, 512, and 612 of cups 204, 304, 404, 504, 604 can be translucent, as discussed previously.

In embodiments, a dimension or dimensions (e.g., volume, opening diameter, height, etc.) of one or more of cups 204, 304, 404, 504, 604 can be different from a corresponding dimension or dimensions of one or more other cups 204, 304, 404, 504, 604. Different cup dimensions can create different chamber geometries which can impact cupping area and/or intensity for a given intensity of pump 120. Accordingly, the user can select a particular one of cups 204, 304, 404, 504, 604 and the user can connect the selected one of cups 204, 304, 404, 504, 604 to therapy unit 102 to control aspects of the cupping therapy based upon the dimensions of the selected one of cups 204, 304, 404, 504, 604.

In embodiments, first cup 204 can have a second opening 210 diameter $D_2$, second cup 304 can have a second opening 310 diameter $D_3$, third cup 404 can have a second opening 410 diameter $D_4$, fourth cup 504 can have a second opening 510 diameter $D_5$, and fifth cup 604 can have a second opening 610 diameter $D_6$. The second opening 210 diameter $D_2$, the second opening 310 diameter $D_3$, the second opening 410 diameter $D_4$, the second opening 510 diameter $D_5$, and the second opening 610 diameter $D_6$ can each be different diameters, the same diameter, or some can be different diameters while others are the same. For example, in embodiments the second opening 210 diameter $D_2$ and the second opening 310 diameter $D_3$ can each be approximately 55 mm, the second opening 410 diameter $D_4$ can be approximately 45 mm, and the second opening 510 diameter $D_5$ and the second opening 610 diameter $D_6$ can each be approximately 35 mm. Other second opening diameters, such as for example 40 mm, are possible.

In embodiments, first cup 204 can have a height $H_2$, second cup 304 can have a height $H_3$, third cup 404 can have a height $H_4$, fourth cup 504 can have a height $H_5$, and fifth cup 604 can have a height $H_6$. The height $H_2$, the height $H_3$, the height $H_4$, the height $H_5$, and the height $H_6$ can each be different, the same, or some can be different heights while others are the same. For example, in embodiments the height $H_2$ and the height $H_5$ can each be approximately 65 mm and the height $H_3$, height $H_4$, and height $H_6$ can each be approximately 55 mm. Other diameters are possible.

Figure 10:
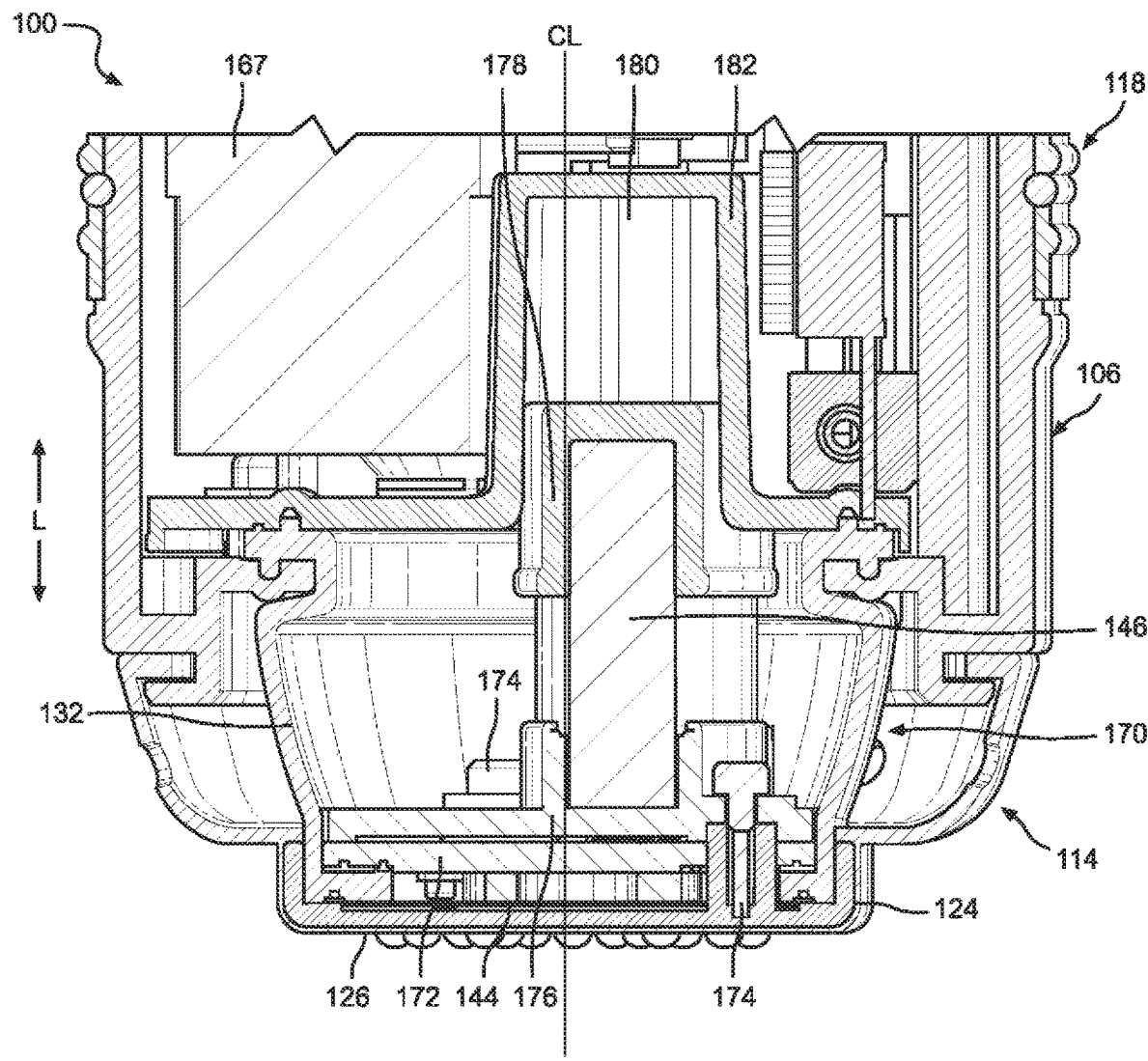
FIG. 10 shows a cross section view along line A-A of the suction assembly of FIG. 1.

FIG. 10 shows a cross section view of the suction assembly 100 shown in FIG. 1. In embodiments such as shown in FIG. 10, the suction assembly 100 can include a vibration assembly 170 that can be connected to the motor 146 and that can movably hold the motor 146 within the housing 106. The vibration assembly 170 can completely or partially surround the motor 146, which together with the low pressure within the cup 104 can suppress sound generated by the motor 146 during vibration therapy. The vibration assembly 170 can include, for example, a plate 172. The plate 172 can have a surface area that is substantially the same (e.g., +/−10%) as a surface area of the contact surface 126. According to this feature, the vibration therapy can be distributed evenly along surface area of the contact surface 126. The plate 172 can be connected with fasteners 174 to a motor bracket 176. The motor bracket 176 can hold the motor 146.

The vibration assembly 170 can include a resilient cap 178, which can be made for example out of rubber, silicone, or any other suitable resilient material. The resilient cap 178 can surround an end of the motor 146 that opposes the motor bracket 176 and that is disposed towards the intermediate portion 118. The resilient cap 178 can move within a cavity 180 of an inner cover 182 of the housing 106. The cavity 180 can have a complementary shape to a shape of the resilient cap 178 that can allow the resilient cap 178 and motor 146 to move freely along the longitudinal direction L but that can restrict movement of the resilient cap 178 and the motor 146 in directions other than the longitudinal direction L. According to this configuration, contact with the skin surface S can be improved. This is because the structural relationship between the resilient cap 178, the motor 146, and the cavity 180 can prevent the vibration assembly 170 and the contact surface 126 connected thereto from moving in directions other than the longitudinal direction L, which can prevent the contact surface 126 from skewing relative to the skin surface S. The cavity 180 and motor 146 can be at least partially offset from a center line CL of the suction assembly 100. This can improve the form factor of the suction assembly 100 for example by evenly distributing the weight and allowing the cavity 180 and motor 146 to be accommodated within the housing 106 without interfering with other structures of the suction assembly such as the power supply 167.

The vibration assembly 170 can include the resilient component 132. The resilient component 132 can be made of silicone, rubber, or any other suitable resilient material. The resilient component 132 can be directly or indirectly connected to any or all of the body 124, heater 144, motor 146, plate 172, motor bracket 176. The resilient component 132 can bias any or all of the body 124, heater 144, motor 146, plate 172, motor bracket 176 towards the extended position and can permit movement of any or all of these structures between the extended, retracted, and intermediate positions in the same manner discussed previously for the body 124 in the description of FIGS. 1, 3, and 4. In embodiments, the resilient component 132 can define a skirt.

Figure 11:
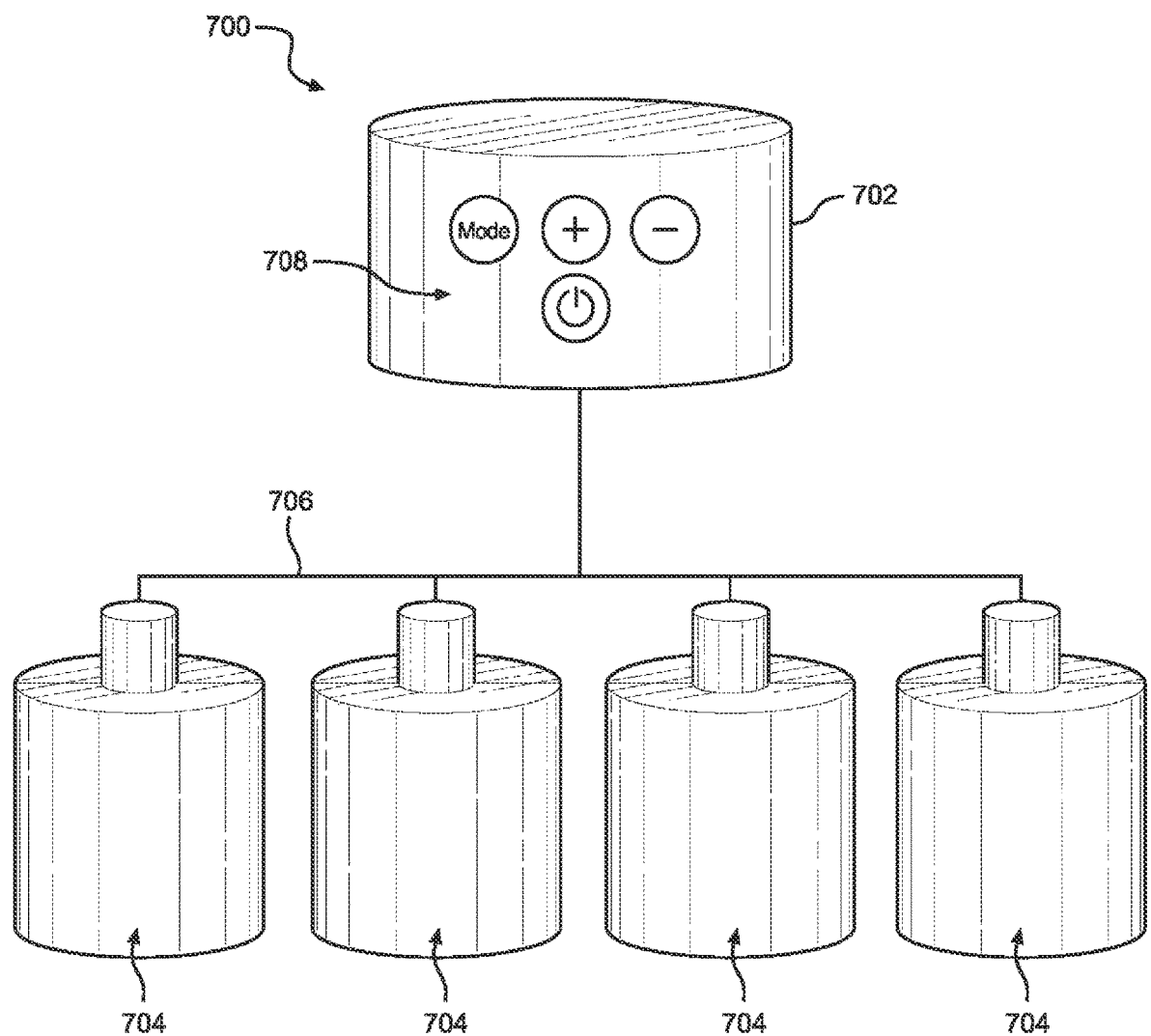
FIG. 11 shows schematic view of another suction assembly.
Figure 12:
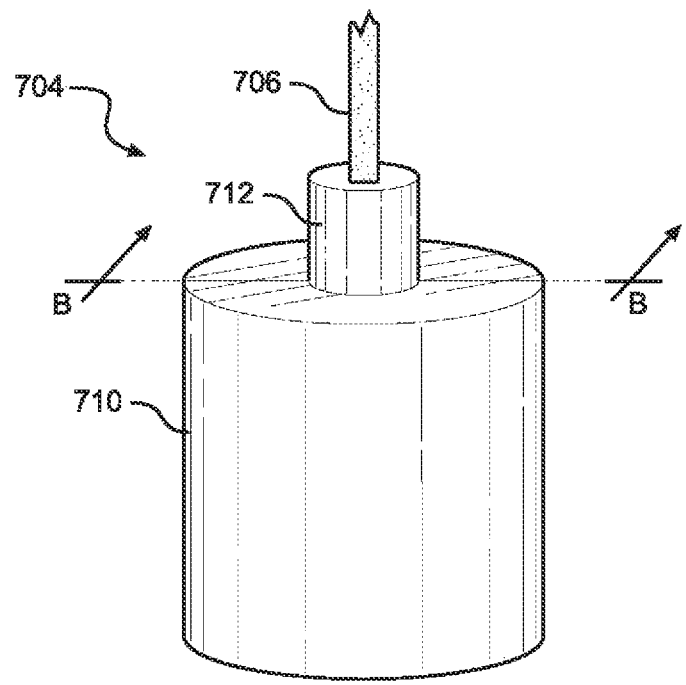
FIG. 12 shows a cup and a supply line of the suction assembly of FIG. 11.
Figure 13:
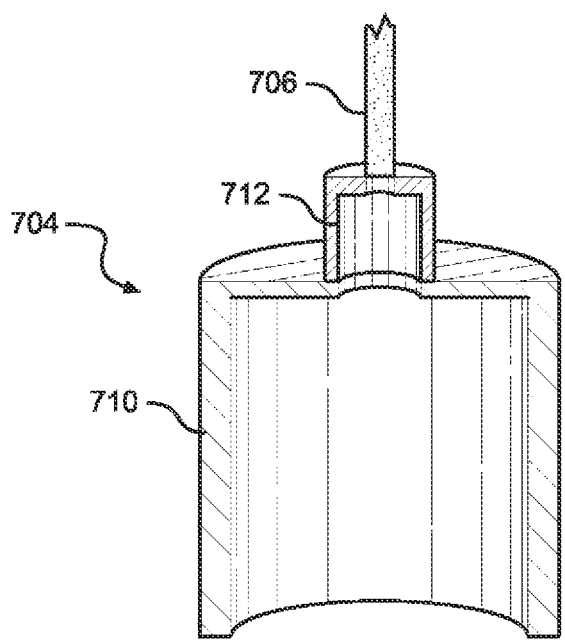
FIG. 13 shows a cross section view along line B-B of the cup and supply line of FIG. 12.

FIGS. 11-13 show views of another suction assembly 700 according to aspects of this disclosure. The suction assembly 700 can include a controller 702 that can be connected to a series of cups 704 by supply lines 706. The supply lines 706 can include tubing, pipes, wires, etc. The supply lines 706 can fluidly and/or electrically connect the controller 702 and the cups 704. The controller 702 can apply a therapy, such as vacuum suction and/or a heat treatment, to one or more of the cups 704. The therapy can be applied in parallel or in series as dictated by the controller 702. The controller 702 can include a therapy source (e.g., a pump and/or heater) to supply the therapy (e.g., suction or heat) to the cups. In embodiments, the cups 704 can be in communication with the controller 702 via supply lines 706. Supply lines 706 can communicate the therapy to the cups 704. For example, the supply lines 706 can reduce the pressure with the cups 704 to initiate a cupping therapy. The supply lines 706 may run from the controller 702 to each of the cups 704 and can branch to connect each of the cups 704 to the controller 702. The controller 702 can include an interface 708 for a user to interface with the controller 702. The interface 708 can include buttons such as a power button, a mode button, and one or more buttons to increase or decrease a magnitude of the therapy.

Any number of cups 704 can be connected to controller 702. Each cup 704 can define a hollow cup body 710, as shown in FIGS. 11 and 12. Cups 704 can include any suitable material, can form any number of sizes for application on a variety of body parts, and/or can be interchangeable. Each of the cups 704 can include a connection 712 through which a supply line 706 can connect to the hollow cup body 710. In embodiments, the connection 712 can have a cylindric body that can share a same central axis as the hollow cup body 710. The connection 712 can include a valve.

The suction assembly embodiments disclosed herein can solve the problems presented by traditional cupping techniques. For example, the suction assembly embodiments of this disclosure can reliably perform cupping therapy alone or together with other therapies. The suction assembly embodiments can be used easily and safely by inexperienced users without the supervision of trained practitioners, and can regulate the cupping therapy and/or other therapies to eliminate or reduce adverse effects of the cupping therapy.

It will be appreciated that the foregoing description provides examples of the disclosed machine. However, it is contemplated that other implementations of the invention may differ in detail from the foregoing examples. All references to the invention or examples thereof are intended to reference the particular example being discussed at that point and are not intended to imply any limitation as to the scope of the invention more generally. All language of distinction and disparagement with respect to certain features is intended to indicate a lack of preference for those features, but not to exclude such from the scope of the invention entirely unless otherwise indicated. All methods described herein can be performed in any suitable order unless otherwise indicated herein or otherwise clearly contradicted by context.

What is claimed is:

1. A suction assembly comprising:
 a therapy unit comprising:
  a housing extending along a longitudinal direction;
  an inlet provided at a first end of the housing;
  an outlet provided at a second end of the housing;
  a pump in fluid communication with the inlet and the outlet; and
  a body provided at the first end of the housing and extending through a bottom surface of the housing, wherein the body is configured to apply a supplemental therapy to a skin surface; and
 a cup that defines a first opening and a second opening, the first opening is configured to be removably connected to an intermediate portion of the housing and the second opening is configured to interface with the skin surface to define a chamber within the cup,
  wherein the body is movable in the longitudinal direction, wherein the pump is configured to reduce a pressure within the chamber to draw the skin surface into the chamber by pumping gas from the chamber into the inlet and exhausting the gas out the outlet, wherein in response to the skin surface being drawn into the chamber the body moves in the longitudinal direction to maintain contact with the skin surface, and wherein the inlet is spaced apart from the bottom surface and disposed between the bottom surface and the intermediate portion.

2. The suction assembly of claim 1, wherein the cup is a first cup and the chamber is a first chamber, and the suction assembly further comprises a second cup that is interchangeable with the first cup, the second cup defines a first opening and a second opening, the first opening of the second cup is configured to be removably connected to the intermediate portion of the housing and the second opening of the second cup is configured to interface with the skin surface to define a second chamber within the second cup.

3. The suction assembly of claim 2, wherein a volume of the first chamber is different than a volume of the second chamber.

4. The suction assembly of claim 2, wherein a diameter of the second opening of the first cup is different than a diameter of the second opening of the second cup.

5. The suction assembly of claim 2, wherein, when the second cup is interchanged with the first cup and the first opening of the second cup is removably connected to the intermediate portion of the housing, the pump is configured to reduce a pressure within the second chamber to draw the skin surface into the second chamber by pumping gas from the second chamber into the inlet and exhausting the gas out the outlet, and wherein in response to the skin surface being drawn into the second chamber the body moves in the longitudinal direction to maintain contact with the skin surface.

6. The suction assembly of claim 1, wherein the body is movable in the longitudinal direction between an extended position, a retracted position, and an intermediate position between the extended position and the retracted position, and the first end and the second end are opposite ends along the longitudinal direction.

7. The suction assembly of claim 6, wherein the body is biased towards the extended position.

8. The suction assembly of claim 1, further comprising a heater operatively connected to the body and configured to heat the body and wherein the supplemental therapy is heat.

9. The suction assembly of claim 8, further comprising a controller that is configured to control the heater to heat at a predetermined intensity.

10. The suction assembly of claim 1, further comprising a motor operatively coupled to the body and configured to vibrate the body and wherein the supplemental therapy is vibration.

11. The suction assembly of claim 10, further comprising a controller that is configured to control the motor at a predetermined intensity.

12. The suction assembly of claim 1, wherein the body includes protrusions and wherein the supplemental therapy is acupressure.

13. The suction assembly of claim 1, further comprising a filter that is removably connected between the inlet and the pump.

14. A suction assembly comprising:
a therapy unit comprising:
a housing extending along a longitudinal direction;
a plurality of inlets provided at a first end of the housing, at least one inlet being disposed at an exterior surface of the housing;
a plurality of outlets provided at a second end of the housing;
a pump in fluid communication with the plurality of inlets and the plurality of outlets; and
a body provided at the first end of the housing and extending through a bottom surface of the housing, wherein the body is configured to apply a supplemental therapy to a skin surface; and
a cup that defines a first opening, a second opening, and a wall between the first opening and the second opening, the first opening is configured to be removably connected to an intermediate portion of the housing and the second opening is configured to interface with the skin surface to define a chamber within the cup, wherein the pump is configured to reduce a pressure within the chamber and to draw the skin surface into the chamber by pumping gas from the chamber into the plurality of inlets and exhausting the gas out the plurality of outlets, wherein the wall of the cup is translucent and the suction assembly is dimensioned to provide a user with a view into the chamber through the wall of the cup that is substantially unobstructed by the housing, and wherein the plurality of inlets are spaced apart from the bottom surface and disposed between the bottom surface and the intermediate portion.

15. The suction assembly of claim 14, wherein the suction assembly is dimensioned such that a width of the cup at the second opening is within a range of plus or minus fifteen percent of a maximum width of the housing to provide the user with the view into the chamber through the wall of the cup that is substantially unobstructed by the housing.

16. The suction assembly of claim 14, wherein the suction assembly is dimensioned such that a maximum height of the suction assembly is between 1.5 and 1.75 times larger than a maximum width of the housing to provide the user with the view into the chamber through the wall of the cup that is substantially unobstructed by the housing.

17. The suction assembly of claim 14, wherein the therapy unit further comprises a plurality of rings at the intermediate portion of the housing that together with the first opening of the cup define a pressure-tight connection between the intermediate portion of the housing and the cup.

18. The suction assembly of claim 17, further comprising a controller that is configured to control a function of the therapy unit in response to a command received from an external device.

19. The suction assembly of claim 18, wherein the external device is a second suction assembly.

20. The suction assembly of claim 14, wherein the cup is a first cup and the chamber is a first chamber, and the suction assembly further comprises a second cup that is interchangeable with the first cup, the second cup defines a first opening and a second opening, the first opening of the second cup is configured to be removably connected to the intermediate portion of the housing and the second opening of the second cup is configured to interface with the skin surface to define a second chamber within the second cup.

21. The suction assembly of claim 20, wherein a volume of the first chamber is different than a volume of the second chamber.

22. The suction assembly of claim 20, wherein a diameter of the second opening of the first cup is different than a diameter of the second opening of the second cup.

23. The suction assembly of claim 1, wherein the body comprises a contact surface with diameter between 30 mm and 38 mm.

24. The suction cup of claim 8, wherein the body comprises a contact surface with a thickness of approximately 0.5 mm +/− 10% that is configured to allow heat transfer between the heater and the skin surface.

\* \* \* \* \*

UNITED STATES PATENT AND TRADEMARK OFFICE
CERTIFICATE OF CORRECTION

PATENT NO. : 11,957,638 B2
APPLICATION NO. : 17/711590
DATED : April 16, 2024
INVENTOR(S) : Solana et al.

It is certified that error appears in the above-identified patent and that said Letters Patent is hereby corrected as shown below:

In the Claims

In Column 15, Claim 24, Line 7, delete "cup" and insert -- assembly --, therefor.

Signed and Sealed this
Fourth Day of June, 2024

Katherine Kelly Vidal
*Director of the United States Patent and Trademark Office*